(12) United States Patent
Rezach

(10) Patent No.: US 8,430,917 B2
(45) Date of Patent: Apr. 30, 2013

(54) BONE ENGAGING IMPLANT WITH ADJUSTMENT SADDLE

(75) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 450 days.

(21) Appl. No.: 12/609,906

(22) Filed: Oct. 30, 2009

(65) Prior Publication Data

US 2011/0106175 A1    May 5, 2011

(51) Int. Cl.
*A61B 17/70* (2006.01)
*A61B 17/86* (2006.01)

(52) U.S. Cl.
USPC ........... 606/306; 606/305; 606/308; 606/257; 606/266; 606/267; 606/328

(58) Field of Classification Search .......... 606/256–257, 606/266–270, 305–308, 319–321, 328; A61B 17/7035, 17/7037
See application file for complete search history.

(56) References Cited

U.S. PATENT DOCUMENTS

| | | | |
|---|---|---|---|
| 4,946,458 A | 8/1990 | Harms et al. | |
| 5,190,543 A | 3/1993 | Schlapfer | |
| 5,520,689 A | 5/1996 | Schlapfer et al. | |
| 5,536,268 A | 7/1996 | Griss | |
| 5,672,176 A | 9/1997 | Biedermann et al. | |
| 5,989,254 A | 11/1999 | Katz | |
| 6,113,601 A * | 9/2000 | Tatar | 606/266 |
| 6,537,276 B2 | 3/2003 | Metz-Stavenhagen | |
| 6,692,500 B2 | 2/2004 | Reed | |
| 6,736,820 B2 | 5/2004 | Biedermann et al. | |
| 6,800,078 B2 | 10/2004 | Reed | |
| 6,837,889 B2 | 1/2005 | Shluzas | |
| 7,559,943 B2 | 7/2009 | Mujwid | |
| 2002/0026193 A1 | 2/2002 | Barker et al. | |
| 2005/0107788 A1* | 5/2005 | Beaurain et al. | 606/61 |
| 2005/0154391 A1 | 7/2005 | Doherty et al. | |
| 2005/0159750 A1 | 7/2005 | Doherty | |
| 2005/0187548 A1 | 8/2005 | Butler et al. | |
| 2005/0261687 A1 | 11/2005 | Garamszegi et al. | |
| 2006/0036242 A1* | 2/2006 | Nilsson et al. | 606/61 |
| 2006/0036244 A1* | 2/2006 | Spitler et al. | 606/61 |
| 2006/0111715 A1* | 5/2006 | Jackson | 606/61 |
| 2007/0043355 A1* | 2/2007 | Bette et al. | 606/61 |

(Continued)

FOREIGN PATENT DOCUMENTS

| | | |
|---|---|---|
| DE | 4107480 | 9/1992 |
| DE | 4243951 | 7/1994 |

(Continued)

*Primary Examiner* — Eduardo C. Robert
*Assistant Examiner* — Julianna Harvey

(57) ABSTRACT

A bone anchor assembly is provided, which may be used in cervical, thoracic, lumbar or sacral areas of the spine or other orthopedic locations. The anchor assembly includes a bone anchor, a receiver mounted to the bone anchor, a saddle within the receiver, and an engaging member. The receiver extends along a central longitudinal axis proximally away from the bone anchor. A rod or other elongated connecting element is received in a passage of the receiver in contact with the saddle, and the engaging member engages the connecting element against the saddle, which engages the saddle against the proximal head of the bone anchor in the receiver. The orientation of the saddle in the receiver is adjustable to correspond to the orientation of the connecting element relative to the central longitudinal axis of the receiver.

20 Claims, 11 Drawing Sheets

U.S. PATENT DOCUMENTS

| | | | |
|---|---|---|---|
| 2007/0088357 A1* | 4/2007 | Johnson et al. | 606/61 |
| 2008/0177260 A1* | 7/2008 | McKinley et al. | 606/60 |
| 2008/0177321 A1* | 7/2008 | Drewry et al. | 606/266 |
| 2008/0195159 A1 | 8/2008 | Kloss et al. | |
| 2008/0306546 A1 | 12/2008 | Zucherman et al. | |

FOREIGN PATENT DOCUMENTS

| | | |
|---|---|---|
| DE | 19605640 | 8/1997 |
| FR | 2925288 | 6/2009 |
| WO | WO 2009/106733 | 9/2009 |

* cited by examiner

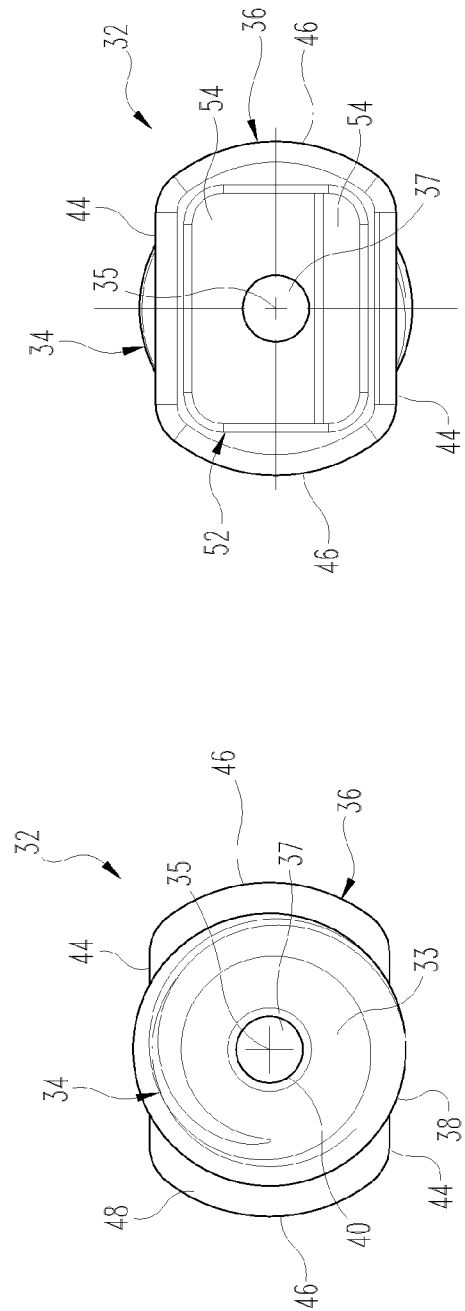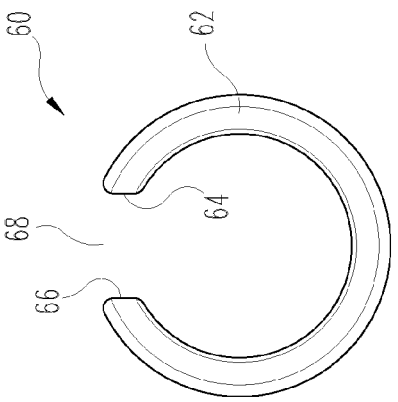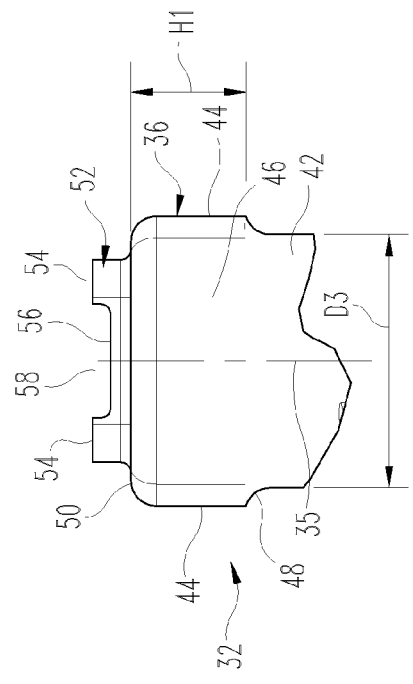

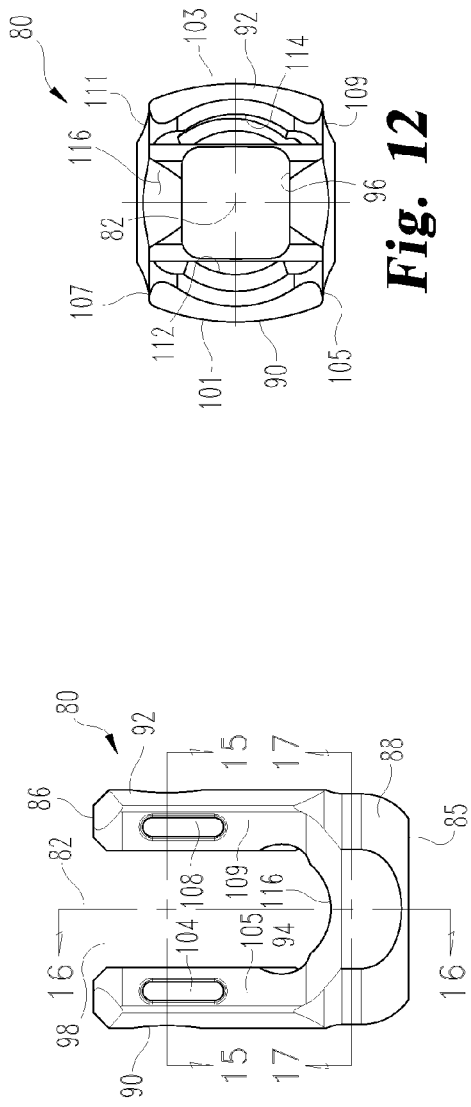

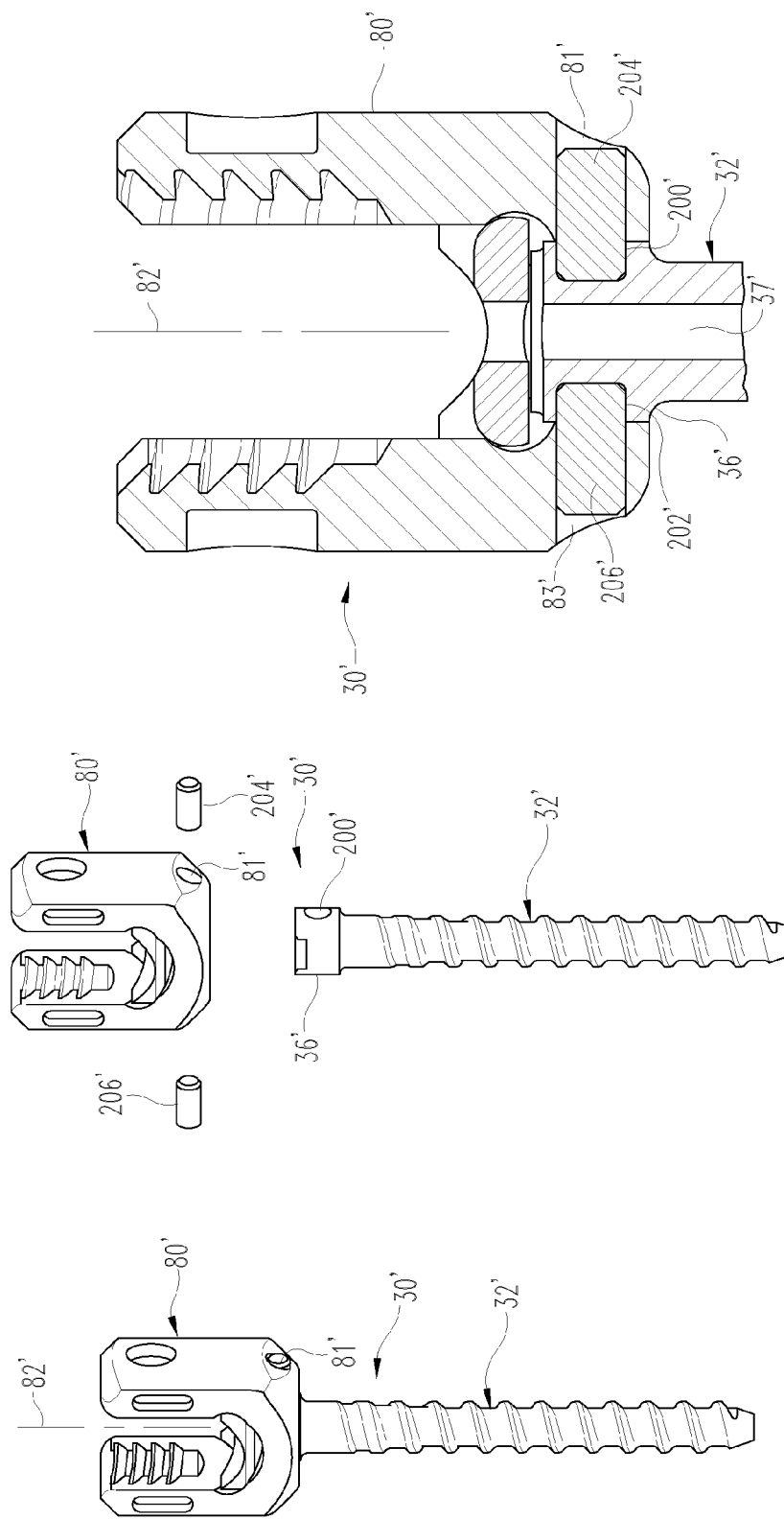

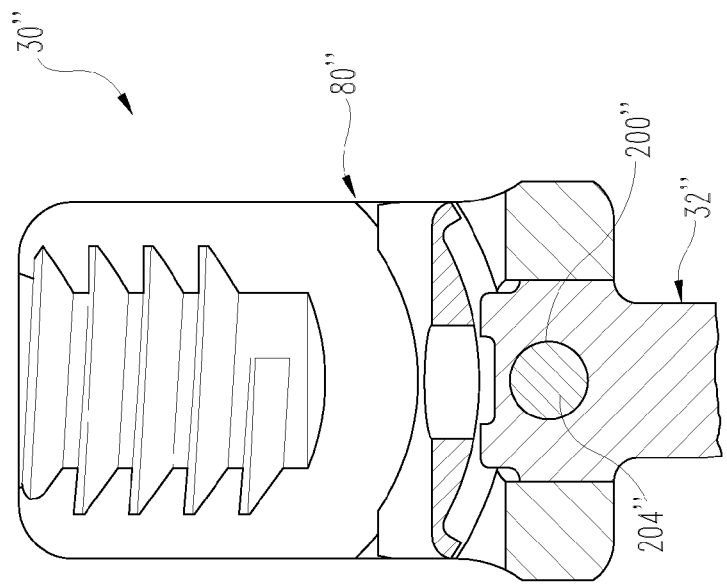
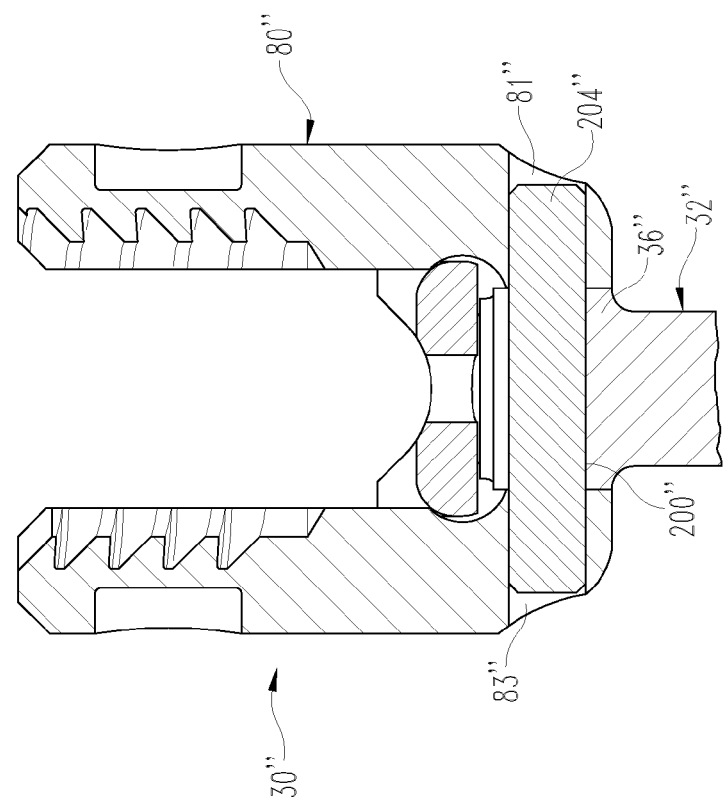

BONE ENGAGING IMPLANT WITH ADJUSTMENT SADDLE

BACKGROUND

The present invention concerns bone anchors and anchor assemblies, particularly useful for engagement to vertebrae. In a particular embodiment, the invention contemplates a bone anchor assembly with an adjustable saddle to secure an elongate connecting element, such as a spinal rod, along the spinal column.

Several techniques and systems have been developed for correcting and stabilizing the spine and for facilitating fusion at various levels of the spine. In one type of system, an elongated rod is disposed longitudinally along the length of the spine or several vertebrae of the spinal column. The rod may be bent to correspond to the normal or desired curvature of the spine in the particular region being instrumented. For example, the rod can be bent or angled to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the lamina of the vertebra. Another type of fixation element is a spinal screw which can be threaded into various aspects of the vertebral bone, such as the pedicle.

In one typical procedure utilizing a bendable, angled, or linear rod, one or more of the rods is situated on one or both of the opposite sides of the spine or spinous processes. A plurality of bone screws are threadingly engaged to several vertebral bodies, such as to the pedicles of these vertebrae. One or more of the bone screws are maneuvered to manipulate the position or orientation of the vertebral body or bodies to which the bone screw is engaged. The rod(s) are connected or affixed to the plurality of bone screws to apply and maintain corrective and stabilizing forces to the spine.

The bone anchors in spinal procedures can have receivers with channels for the elongated rod or other member that, in some bone anchors, open upward, i.e. directly away from the bone to which the anchor is attached. Other bone anchors utilize channels that open along the medial or lateral side of the anchor to receive the rod. The relative positions of the vertebra and the bone anchor receiving the spinal rod to be positioned in the bone anchor may require contouring, bending, and/or angling of the rod through the channel of the bone anchor, which can result in a less than optimal fit between the anchor and the rod, creating undesirable stress concentrations in the rod, bone anchor and/or bony structure. Additional improvements in the bone anchor and rod interface in spinal systems are still needed.

SUMMARY

A bone anchor assembly is provided, which may be used in cervical, thoracic, lumbar or sacral areas of the spine or other orthopedic locations. The anchor assembly includes a bone anchor, a receiver mounted to the bone anchor, a saddle within the receiver, and an engaging member. The receiver extends along a central longitudinal axis proximally away from the bone anchor. A rod or other elongated connecting element is received in a passage of the receiver in contact with the saddle, and the engaging member engages the connecting element against the saddle, which engages the saddle against the proximal head of the bone anchor in the receiver. The orientation of the saddle in the receiver is adjustable to correspond to the orientation of the connecting element relative to the central longitudinal axis of the receiver.

According to a further aspect, a bone anchor assembly for spinal stabilization is provided. The bone anchor assembly includes a receiver extending along a central longitudinal axis between a proximal end and an opposite distal end. The receiver includes a distal portion defining a receptacle and a pair of arms extending from the distal portion along the central longitudinal axis on opposite sides of a passage of the receiver. The receiver includes a bottom surface extending along the passage between the pair of arms. The passage opens at opposite sides of the receiver between the pair of arms and the receptacle opens into the passage and at the distal end of the receiver. The assembly also includes a bone anchor with a distal bone engaging portion and a head at a proximal end of the distal bone engaging portion with the head positioned in the receptacle and the bone engaging portion in a first orientation relative to the central longitudinal axis of the receiver. The assembly also includes a saddle positioned in the passage of the receiver adjacent to the bottom surface of the receiver. The saddle includes a proximal support surface and a distal surface opposite the proximal support surface with the distal surface contacting the head of the bone anchor. The assembly includes a connecting element extending along a longitudinal axis that is located in the passage through the opposite sides of the receiver. The assembly includes an engaging member engaged to the pair of arms to secure the connecting element against the proximal support surface of the saddle. The saddle engages the receiver and is limited to movement in the receiver in a single plane defined by the central longitudinal axis of the receiver and the longitudinal axis of the connecting element while the bone engaging portion remains in the first orientation.

According to another aspect, a bone anchor assembly includes a receiver extending along a central longitudinal axis between a proximal end and an opposite distal end. The receiver includes a distal portion defining a receptacle and a pair of arms extending from the distal portion along the central longitudinal axis on opposite sides of a passage with the passage opening at opposite sides of the receiver. The receiver includes a bottom surface extending along the passage between the pair of arms and the receptacle opens into the passage and at the distal end of the receiver. The assembly includes a bone anchor with a distal bone engaging portion and a head at a proximal end of the distal bone engaging portion with the head positioned in the receptacle with the bone engaging portion extending through the distal end of the receiver in a first orientation relative to the central longitudinal axis of the receive. The head includes a platform extending through the opening of the receptacle into the passage. The assembly also includes a saddle positioned in the passage of the receiver adjacent to the bottom surface of the receiver. The saddle includes a proximal support surface and a distal surface opposite the proximal surface with the distal surface contacting the platform of the head of the bone anchor. The assembly also includes a connecting element extending along a longitudinal axis that is located in the passage against the proximal support surface of the saddle and projecting through the opposite sides of the receiver. An engaging member engages the pair of arms in contact with the connecting element to secure the connecting element against the proximal support surface of the saddle.

According to another aspect, a bone anchor assembly includes a receiver extending along a central longitudinal axis between a proximal end and an opposite distal end. The receiver includes a distal portion defining a receptacle and a pair of arms extending from the distal portion along the central longitudinal axis on opposite sides of a passage that opens at opposite sides of the receiver. The receiver includes a bottom surface extending along the passage between the pair of arms and the receptacle opens into the passage and at the distal end of the receiver. The assembly includes a bone anchor with a distal bone engaging portion and a head at a proximal end of the distal bone engaging portion. The head is positioned in the receptacle with the bone engaging portion extending through the distal end of the receiver in a first orientation relative to the central longitudinal axis of the receiver. The assembly also includes a saddle positioned in the passage of the receiver adjacent to the bottom surface of the receiver. The saddle includes a proximal support surface and a distal surface opposite the proximal support surface. The distal surface contacts the head of the bone anchor. The proximal support surface and the distal surface extend between opposite ends of the saddle and each of the opposite ends of the saddle includes a tooth extending distally from the distal surface of the saddle. The assembly also includes a connecting element extending along a longitudinal axis and the connecting element is located in the passage through the opposite sides of the receiver. An engaging member engages the pair of arms and secures the connecting element against the proximal support surface of the saddle. A respective one of the teeth of the saddle contacts the proximal head of the bone anchor when the saddle is pivoted in the receiver to a maximum angle from an orthogonal orientation of the longitudinal axis of the connecting element with the central longitudinal axis of the receiver.

These and other aspects are discussed further below.

BRIEF DESCRIPTION OF THE FIGURES

FIG. 7 is an elevation view of the distal end of the bone anchor of FIG. 4.

FIG. 8 is an elevation view of the proximal end of the bone anchor of FIG. 4.

FIG. 9 is an enlarged view of the proximal portion of the bone anchor of FIG. 4.

FIG. 10 is a plan view of a retaining member of the bone anchor assembly.

FIG. 11 is an elevation view of a receiver of the bone anchor assembly.

FIG. 12 is a top plan view of the receiver of FIG. 11.

FIG. 13 is a side elevation view of the receiver of FIG. 11.

FIG. 14 is a section view along line 14-14 of FIG. 13.

FIG. 24 is a perspective view of another embodiment bone anchor assembly.

FIG. 25 is a partially exploded perspective view of the bone anchor assembly of FIG. 24.

FIG. 26 is a section view of a portion of the bone anchor assembly of FIG. 24.

FIG. 27 is a longitudinal section view of another embodiment of the bone anchor assembly of FIG. 24.

FIG. 28 is a longitudinal section view of the bone anchor assembly of FIG. 27 along a plane orthogonal to the plane of the section of FIG. 27.

DESCRIPTION OF THE ILLUSTRATED EMBODIMENTS

Figure 1:
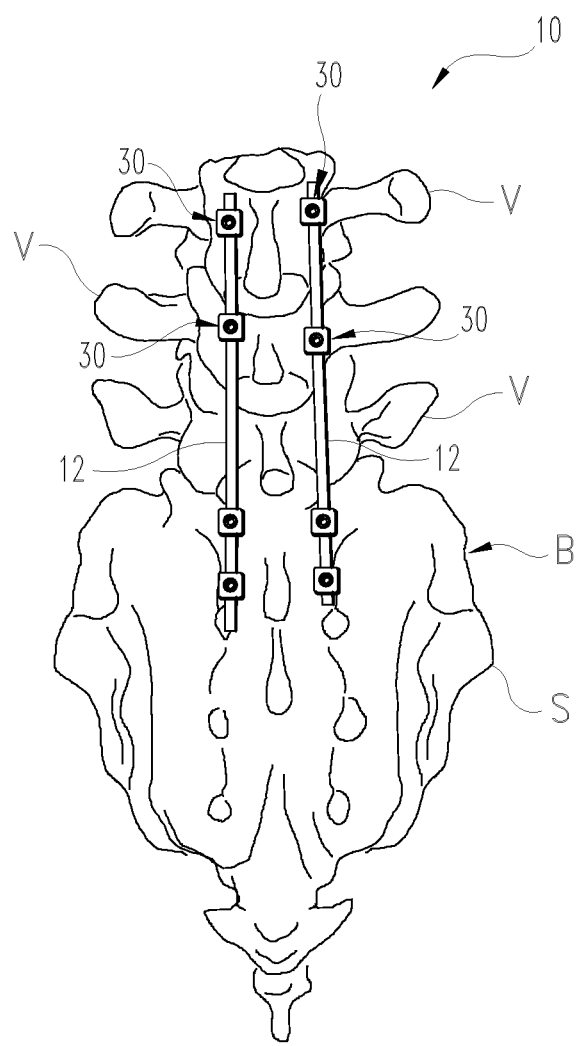
FIG. 1 is a posterior elevation view of a spinal column segment with a spinal implant system engaged thereto.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

FIG. 1 illustrates a posterior spinal implant system 10 located along a spinal column of a patient. Implant system 10 generally includes several bone anchor assemblies 30 with at least one elongated connecting element 12 structured to selectively interconnect two or more bone anchors. Connecting elements 12 may be a spinal rod, plate, bar, or other elongated element having a length to extend between at least two vertebrae. Spinal implant system 10 may be used for, but is not limited to, treatment of degenerative spondylolisthesis, fracture, dislocation, scoliosis, kyphosis, spinal tumor, and/or a failed previous fusion. More specifically, in one embodiment implant system 10 is affixed to posterior elements, such as the pedicles of vertebra V, or other bones B of the spinal column segment, from a posterior approach. Bones B can include the sacrum S and/or one or more of several vertebrae V. Spinal implant system 10 can be engaged to vertebrae of one or more levels of the sacral, lumbar, thoracic and/or cervical regions of the spinal column. Other embodiments contemplate that spinal implant system 10 is engaged along other portions of the spine, such as the anterior, lateral or oblique portions of the vertebrae V. Still other embodiments contemplate applications in procedures other the spinal stabilization procedures.

Figure 2:
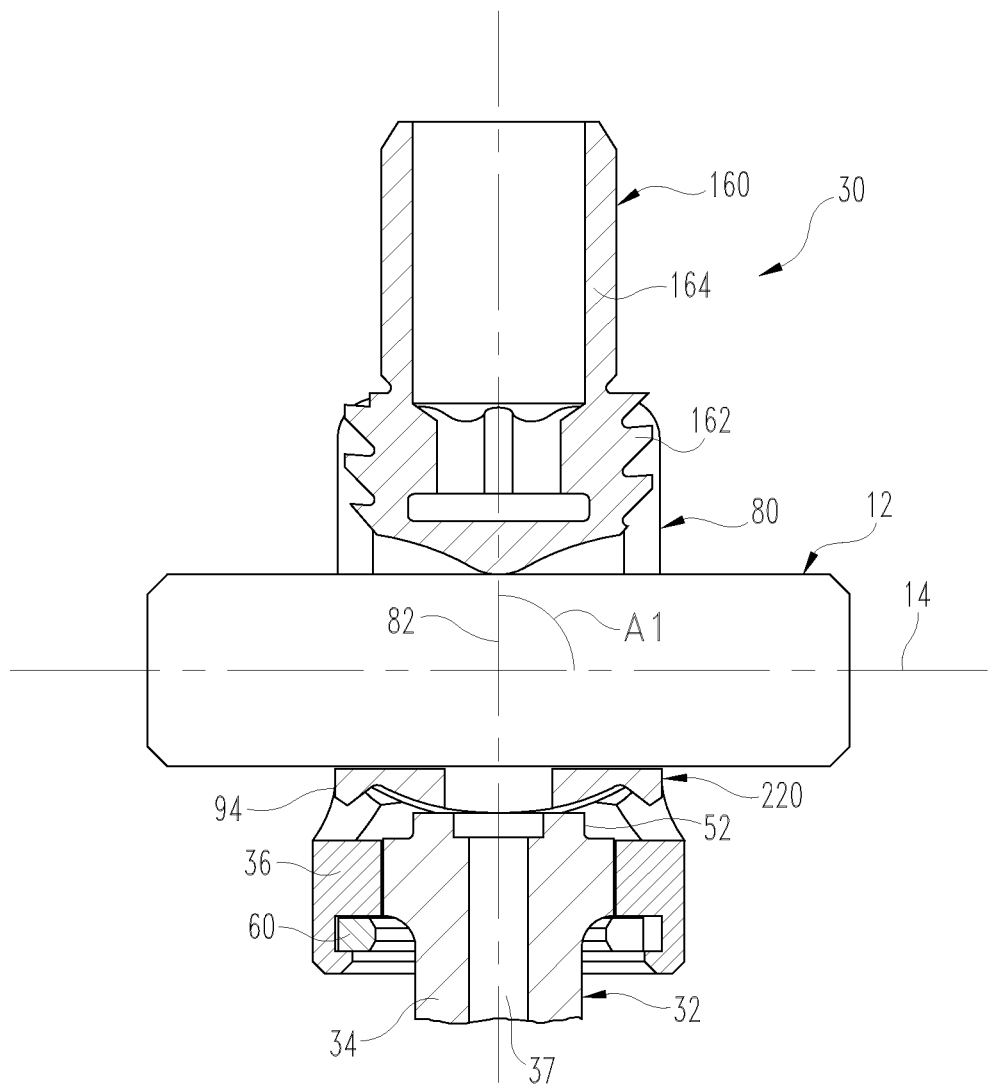
FIG. 2 is a partial sectional view of one embodiment of a bone anchor assembly with the connecting element in a first orientation relative to the bone anchor.
Figure 3:
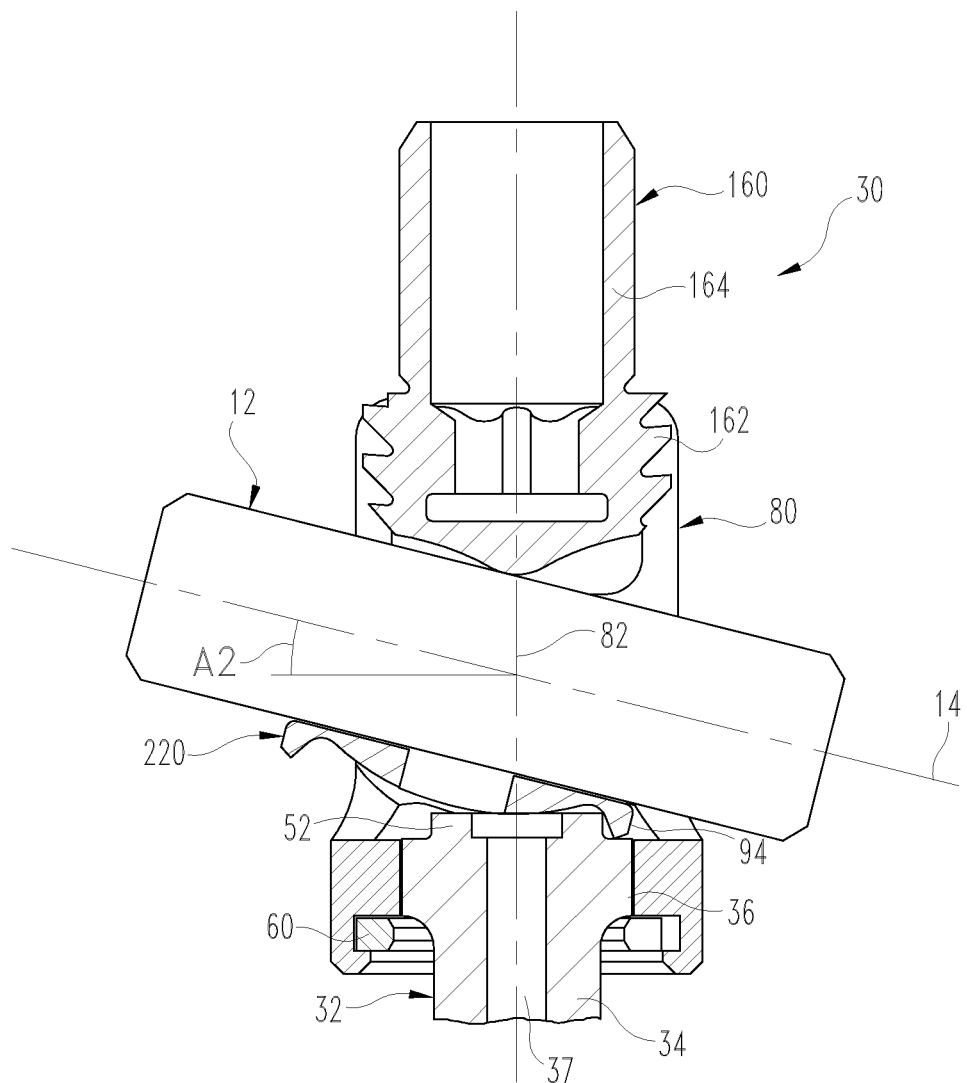
FIG. 3 is a partial sectional view of the bone anchor assembly of FIG. 2 with the connecting element in a second orientation relative to the bone anchor.
Figure 4:
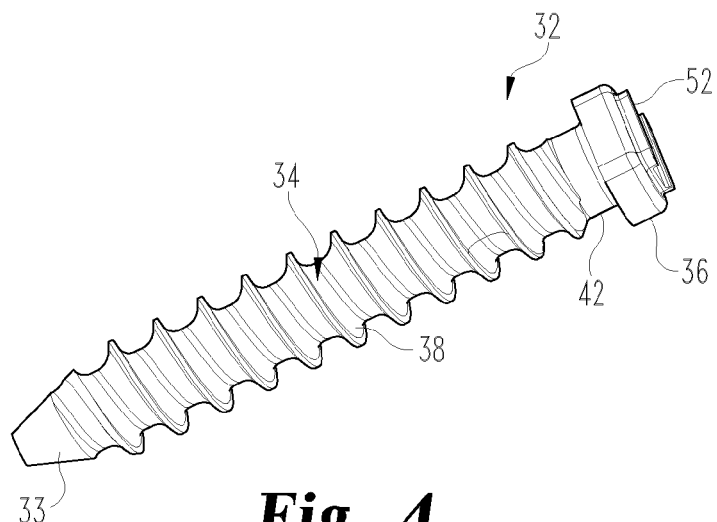
FIG. 4 is a perspective view of a bone anchor comprising a portion of the bone anchor assembly.
Figure 5:
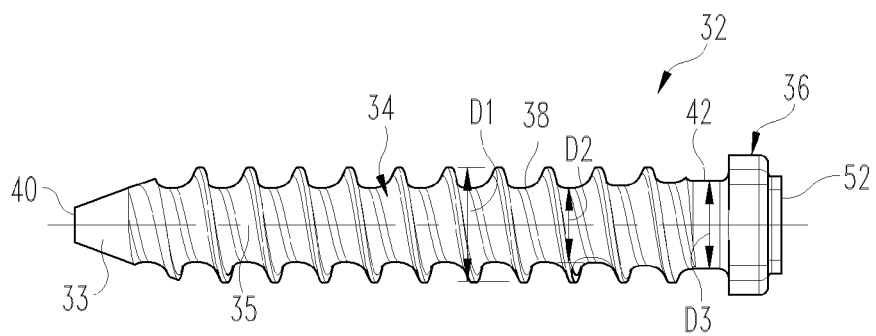
FIG. 5 is an elevation view of the bone anchor of FIG. 4.
Figure 6:
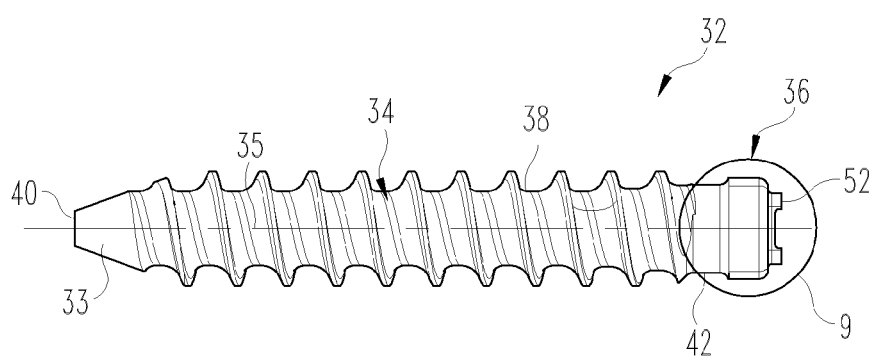
FIG. 6 is another elevation view of the bone anchor of FIG. 4 rotated 90 degrees about its longitudinal axis from its FIG. 5 orientation.

Referring to FIGS. 2-3, there is shown a longitudinal section view of a portion of one embodiment of bone anchor assembly 30 and connecting element 12 projecting from opposite sides of the bone anchor assembly 30. Bone anchor assembly 30 includes a bone anchor 32 with a distal bone engaging portion 34 configured for attachment to a vertebra, such as cervical, thoracic, lumbar and/or sacral vertebrae, or other bones or tissues in the body of a patient. Bone anchor assembly 30 also includes a receiver 80 coupled to bone anchor 32 with retaining member 60. Receiver 80 includes a passage extending through opposite sides of receiver 80 that receives connecting element 12 in a transverse orientation to bone anchor 32. An adjustable saddle 220 is located in receiver 80 between a proximal head 36 of bone anchor 32 and connecting element 12. Saddle 220 supports connecting element 12 in receiver 80 and pivots in a plane defined by the central longitudinal axis 14 of connecting element 12 and a central longitudinal axis 82 of receiver 80. Saddle 220 supports connecting element 12 and maintains a proximal support surface of saddle 220 in contact with connecting element 12 at various orientations of longitudinal axis 14 relative to longitudinal axis 82 that vary from an orthogonal orientation A1, such as shown in FIG. 2, to a maximum angular orientation A2, such as shown in FIG. 3. In one embodiment, angle A2 is 30 degrees from the orthogonal orientation 14' of connecting element 12. Other embodiments contemplate angle A2 ranging from more than 0 degrees to about 45 degrees. The orientation of connecting element 12 and saddle 220 can vary at angle A2 relative to longitudinal axis 82 while the orientation between receiver 80 and bone anchor 32 is maintained in a fixed or substantially fixed relationship. As saddle 220 is pivoted toward the maximum angular orientation, one end of saddle member 220 can project outwardly from passage 94 through the adjacent end of receiver 80, as shown in FIG. 3. Engaging member 160 is engaged to receiver 80 and secures connecting element 12 in receiver 80 against saddle 220 in the selected or desired orientation.

FIGS. 4-9 show additional views of bone anchor 32. Bone anchor 32 described herein can be included with bone engaging portion 34 configured as a bone screw, vertebral hook, bone clamp, and or other suitable bone engaging arrangement. Bone anchor 32, in the embodiment shown in FIG. 2, includes an elongated bone engaging portion 34 extending from a distal end portion 33 along a central longitudinal axis 35 to a proximal head 36 that is centered on central longitudinal axis 35. Bone engaging portion 34 is shown with an elongated shaft 38 having one or more threads along at least a portion thereof. The threads may be cancellous threads with the shaft sized and configured for implantation into a vertebra or other bone. The threads of bone engaging portion 34 may be self-tapping, self-drilling, continuous, intermittent, of multiple thread forms, or other appropriate configurations. Furthermore, bone anchor 32 may include a lumen 37 as shown in FIGS. 2-3, or be solid. Lumen 37 extends through the proximal and distal ends of anchor 32 for receipt of guidewire and/or injection of material into the bone. One or more fenestrations may be provided along bone engaging portion 34 of bone anchor 32 that communicate with lumen 37.

Bone anchor 32 includes elongated shaft 38 extending proximally and distally along longitudinal axis 35 between head 36 and distal end portion 33. Distal end portion 33 includes a flat distal end 40, and tapers outwardly from distal end 40 along a frusto-conically shaped end portion 33 to a threaded portion of shaft 38. The threaded portion of shaft 38 includes a helical thread with a major diameter D1 and a minor diameter D2 that are constant along a major length of shaft 38 from distal end portion 33 to a transition portion 42 between shaft 38 and head 36. Transition portion 42 includes a smooth and circular outer surface extending around shaft 38 that defines a third diameter D3 that is greater than minor diameter D2 and less than major diameter D1. The helical thread runs out at transition portion 42. Other embodiments contemplate other configurations for the thread profile and shaft 38, including those with varying diameters and profiles along the length of shaft 38.

As further shown in FIGS. 7-9, head 36 includes a rectangular shape with linear elongated sides 44 and rounded shorter sides 46 extending between the elongated sides 44. Head 36 includes elongated sides 44 that project outwardly from the major diameter of shaft 38. Shorter sides 46 have a length that is greater than diameter D3 of transition portion 42 and less than that of major diameter D1 of shaft 38. Shorter sides 46 are convexly curved between longer sides 44, and longer sides 44 are linear between shorter sides 46. Head 36 forms a distally oriented lip 48 that projects outwardly from transition portion 42, and lip 48 projects outwardly a greater amount at shorter sides 46, as shown in FIG. 7, than at longer sides 44, as shown in FIG. 9. Head 36 includes a height H1 extending from transition portion 42 to a proximal surface 50. Head 36 also includes a rectangular platform 52 extending proximally from proximal surface 50. Platform 52 is confined between sides 44, 46 of head 36. Platform 52 includes a pair of elongated rails 54 extending along longer sides 44, and tie 56 extending between rails 54. Tie 56 is recessed distally relative to rails 54 to form a proximally opening groove 58. Groove 58 also opens at the ends of rails 54 toward shorter sides 46. Lumen 37 opens proximally through tie 56 into groove 58 at the proximal side of platform 52.

FIG. 10 shows retaining member 60 that couples bone anchor 32 to receiver 80. Retaining member 60 includes a circular, ring-shaped body 62 extending between ends 64, 66 having a gap 68 therebetween. Gap 68 allows the outer dimension of ring 60 to be compressed and reduced for positioning in a groove 84 extending around receiver 80, and then resiliently returns toward a non-compressed state to engage the groove 84 in receiver 80. Ring 60 extends around transition portion 42 of bone anchor 32 and extends outwardly from the groove 84 in receiver 80 to contact and support head 36 at lip 48 on the distal side of head 36. In particular, the portions of lip 48 extending from shorter sides 46 to transition portion 42 are supported on retaining member 60, while longer sides 44 each form a chord that extends through the interior of retaining member 60.

FIGS. 11-17 show further details of receiver 80. Receiver 80 includes a U-shaped body extending along central longitudinal axis 82 between a distal end 85 and a proximal end 86. Receiver 80 includes a distal bowl portion 88 extending proximally from distal end 85, and a pair of arms 90, 92 extending proximally from distal bowl portion 88 on opposite sides of longitudinal axis 82 to proximal end 86. Arms 90, 92 define a passage 94 therebetween that opens at opposite sides of arms 90, 92 to receive connecting element 12 in a transverse orientation to longitudinal axis 82. Bowl portion 88 defines a receptacle 96 that opens into passage 94 and extends from passage 94 through distal end 84. Arms 90, 92 also define a proximal opening 98 at proximal end 86 that extends along arms 90, 92 to passage 94. Engaging member 160 is engaged to receiver 80 through the proximal end opening to contact connecting element 12 in passage 94.

Arms 90, 92 each include a circular recess 100, 102 in the outer side surface 101, 103, respectively, thereof that face opposite directions from one another. Arm 90 also includes oblong recesses 104, 106 in each of the opposite end surfaces 105, 107 thereof. Arm 92 similarly includes oblong recesses 108, 110 in each of the opposite end surfaces 109, 111 thereof. The recesses provide locations in which various tools and instrumentation can be engaged and mounted to receiver 80 to facilitate implantation and maneuvering of bone anchor 30 and connecting element 12 in the patient. End surfaces 105, 107 and end surfaces 109, 111 each are elongated in a longitudinal direction in a parallel orientation to longitudinal axis 82, and extend between the respective outer side surface 101, 103 to the respective inner surface 112, 114 of arms 90, 92 in an orthogonal orientation to longitudinal axis 82. Each of the inner surfaces 112, 114 includes a central concavely curved portion and linear end portions that between the respective end surfaces 105, 107 and end surfaces 109, 111. The central concave portion of inner surface 112, 114 defines a thread profile to threadingly engage engaging member 160. Each thread profile extends along longitudinal axis 82 from proximal end 86 of arms 90, 92 to a location adjacent to passage 94 in receiver 80.

Figure 16:
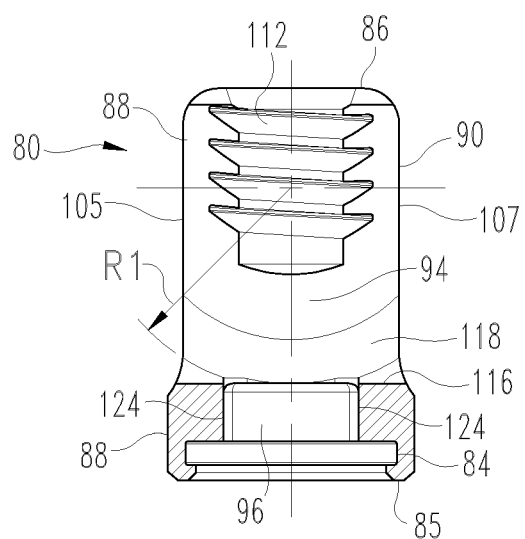
FIG. 16 is a section view along line 16-16 of FIG. 11.

Receiver 80 includes a bottom surface 116 that extends between inner surfaces 112, 114 of arms 90, 92 along the distal side of passage 94. Receptacle 96 opens through bottom surface 116. In addition, each of the arms 90, 92 includes a groove 118, 120, respectively, formed in the respective inner surface 112, 114 thereof along bottom surface 116. Each groove 118, 120 extends from one of the end surfaces 105, 109 of the respective arm 90, 92 to the other end surface 107, 111 of the respective arm 90, 92. As shown in FIG. 16 with respect to groove 118, each groove 118, 120 is curved between the respective end surfaces of the arm in which it is formed with the distal side of the groove defined by a radius R so that the middle of the curved groove is located more distally than the opposite ends of the groove. As shown in FIG. 14, the distal sides of the grooves 118, 120 intersect receptacle 96 adjacent the middle portions of the grooves 118, 120. Grooves 118, 120 extend from the middle portion thereof so that the opposite ends of grooves 118, 120 are spaced proximally from bottom surface 116 where the groove exits at the opposite end surfaces 105, 107 or end surfaces 109, 111 of the respective arm 90, 92. Grooves 118, 120 are concavely curved in the respective inner surface 112, 114 to form a C-shape as shown in FIG. 14.

Figure 15:
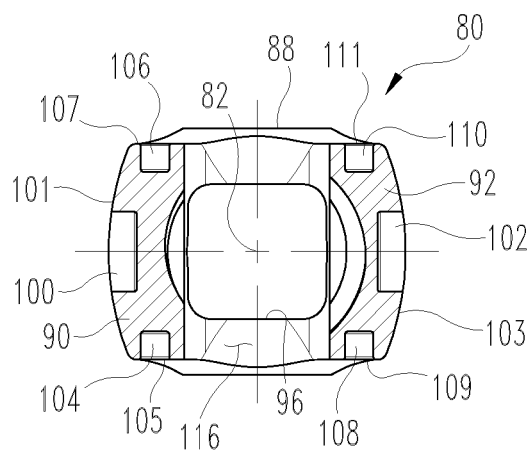
FIG. 15 is a section view along line 15-15 of FIG. 11.
Figure 17:
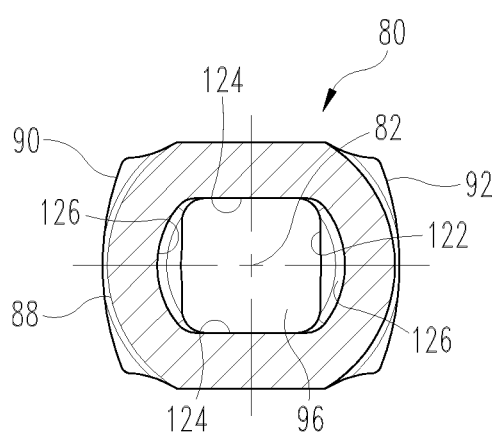
FIG. 17 is a section view along line 17-17 of FIG. 11.

As shown in FIGS. 12 and 15, receptacle 96 includes a square shaped opening through bottom surface 116 defined by lip 122 extending around the proximal side of receptacle 96. Platform 52 of bone anchor 32 is sized to extend the square-shaped opening to contact saddle 220 positioned along bottom surface 116. As shown in FIG. 17, receptacle 96 includes a shape that corresponds to the rectangular shape of head 36, and includes elongated, linear sides 124 connected with concavely rounded shorter sides 126 extending between the longer sides 124. Head 36 fits in receptacle 96 with longer sides 44 extending along longer sides 124 of receptacle 96 and with convexly rounded shorter sides 46 positioned along concave sides 126. The longer sides 124 are oriented to extend in the direction between arms 90, 92, and the shorter sides 126 are oriented to extend in the direction of passage 94. Lip 122 sits on the proximal surface 50 of head 36 at the portion extending outwardly from platform 52 to rounded sides 46, while platform 52 extends through the opening into passage 94. The interface of head 36 in receiver 80 prevents rotation of receiver 80 around central longitudinal axis 82 relative to head 36, while permitting some limited side-to-side toggling of receiver 80 in the directions toward shorter sides 46 and in the directions toward longer sides 44.

Figure 20:
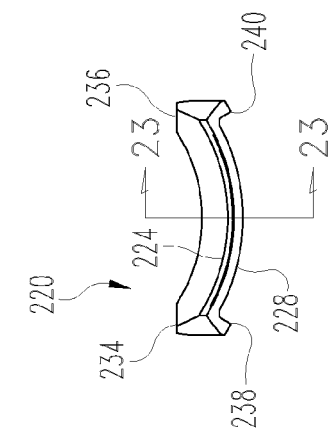
FIG. 20 is a side elevation view of the saddle of FIG. 18.
Figure 19:
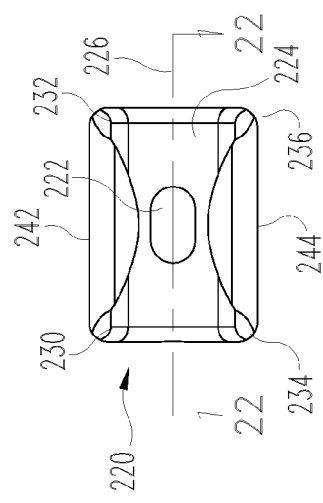
FIG. 19 is a top plan view of the saddle of FIG. 18.
Figure 18:
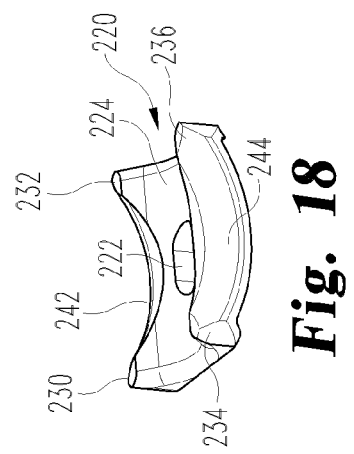
FIG. 18 is a perspective view of a saddle comprising a portion of the bone anchor assembly.
Figure 23:
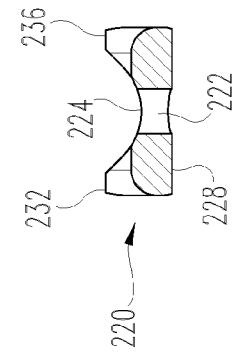
FIG. 23 is a section view along line 23-23 of FIG. 20.
Figure 22:
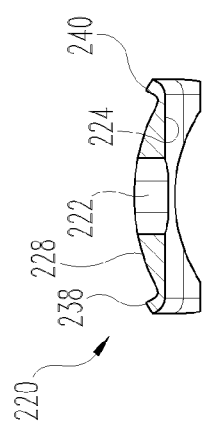
FIG. 22 is a section view along line 22-22 of FIG. 19.
Figure 21:
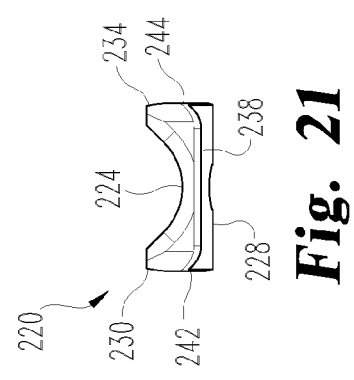
FIG. 21 is an end elevation view of the saddle of FIG. 18.

FIGS. 18-23 show various view of saddle 220. Saddle 220, as shown in FIGS. 2-3, is positioned in receiver 80 between connecting element 12 and head 36 of bone anchor 32. Saddle 220 includes a body with a rectangular shape when saddle 220 is viewed in a proximal to distal direction, as shown in FIG. 19. Saddle 220 extends along a longitudinal axis 226 between opposite ends, and includes an oblong hole 222 extending through a center thereof between upper and lower surfaces thereof. Hole 222 aligns with lumen 37 of bone anchor 32. The oblong shape of hole 222 allows at least a portion of hole 222 to align with lumen 37 even if saddle 220 is pivoted to a non-centered position in receiver 80. Saddle 220 includes a proximal support surface 224 against which connecting element 12 is positioned. Proximal support surface 224 is linear in a direction paralleling longitudinal axis 226 as shown in FIG. 22, and is concavely curved orthogonally to longitudinal axis 226 as shown in FIGS. 21 and 23. The shape of proximal support surface 224 matches the shape of the portion of the outer surface of connecting element 12 positioned thereagainst.

Saddle 220 includes a distal surface 228 opposite proximal surface 224. Distal surface 228 is convexly curved along longitudinal axis 226 as shown in FIGS. 20 and 22, and is linear between the opposite sides of saddle 220, as shown in FIGS. 21 and 23. Distal surface 228 contacts and is supported by platform 52 of head 36 of bone anchor 32. The convexly curved distal surface 228 facilitates pivoting movement of saddle 220 in the plane that includes longitudinal axis 82 of receiver 80 and longitudinal axis 14 of connecting element 12. In addition, saddle 220 includes ears 230, 232, 234, 236 extending outwardly from proximal support surface 224 that are received in respective ones of the grooves 118, 120 of receiver 80. Ears 230, 232 are positioned in and translate along groove 118, and ears 234, 236 are positioned in and translate along groove 120 as saddle 220 pivots in receiver 80 in the plane defined by longitudinal axis 82 of receiver 80 and longitudinal axis 14 of connecting element 12. Ears 230, 232, 234, 236 maintain saddle 220 within receiver 80 along a path defined by grooves 118, 120 and prevent saddle 220 from pivoting or twisting to an undesired orientation in receiver 80.

Saddle 220 also includes a first tooth 238 at one end thereof that extends between ears 230, 234 and projects distally from distal surface 228, and saddle 220 includes a second tooth 240 at the opposite end thereof that extends between ears 232, 236 and projects distally from distal surface 228. Saddle 220 includes a first elongate side 242 extending between ears 230, 232 with a proximal side that is concavely curved between ears 230, 232 and an opposite convexly curved distal side between ears 230, 232. Saddle 220 also includes a second elongate side 244 extending between ears 234, 236 with a proximal side that is concavely curved between ears 234, 236 and an opposite convexly curved distal side between ears 234, 236. The curvature of sides 242, 244 corresponds to the curvature of the respective groove 118, 120 so that saddle 220 extends across bottom surface 116 of receiver 80 into the grooves 118, 120. Convexly curved distal surface 228 contacts rails 54 of platform 52 and slides along rails 54 as saddle 220 translates in grooves 118, 120. When saddle 220 is sufficiently pivoted in receiver 80 to a maximum angle A2, one of the first and second teeth 238, 240 contacts an adjacent side of platform 52 to prevent further pivoting movement of saddle 220 in receiver 80, as shown in FIG. 3.

Referring to FIGS. 2-3, engaging member 160 is movably engaged to arms 90, 92 of receiver 80 through the proximal end opening 98 of receiver 80. Engaging member 160 is movable toward passage 94 by threading it along arms 90, 92 of receiver 36 to contact connecting element 12 and direct connecting element 12 into receiver 80 and into engagement with proximal support surface 224 of saddle 220, which in turn moves and/or forces distal surface 228 of saddle 220 into contact with platform 56 of anchor 32, securing connecting element 12 and anchor 32 to one another and securing anchor 32 against retaining member 60 of receiver 80. In the illustrated embodiment, engaging member 160 is a set screw type element with an externally threaded body 162 that threadingly engages inner threads provided along arms 90, 92. Other embodiments contemplate an engaging member in the form of a nut, cap, or combination of nut and set screw. In still other embodiments, engaging member 160 engages receiver 80 in a non-threaded manner, such as a friction fit, interference fit, or bayonet lock. Engaging member 160 also includes a proximal break-off portion 164 extending from body 162 to facilitate engagement of engaging member 160 to receiver 80 and in the application of sufficient force to secure the assembly of connecting element 12 against saddle 220 and saddle 220 against anchor 32. Break-off portion 164 is severed upon application of a threshold torque that provides the desired level of fixation of anchor assembly 30.

Referring now to FIGS. 24-26, bone anchor assembly 30' is similar to bone anchor assembly 30, but includes another embodiment means for securing the receiver to the bone anchor. Bone anchor 32' includes a proximal head 36' with opposite detents 200', 202' formed in each of the longer sides of the rectangular shaped head. Receiver 80' includes opposite holes 81', 83' adjacent the distal side thereof that aligns with respective ones of the detents 200', 202'. A first pin 204' is positioned in hole 81' and detent 200' and a second pin 206' is positioned in hole 83' and detent 202'. Pins 204', 206' pivotally couple receiver 80' to head 36' to limit pivoting of receiver 80' to pivoting movement around pins 204', 206' in the plane defined by the longitudinal axis 82' of receiver 80' and longitudinal axis 14 of connecting element 12. Pins 204', 206' define a pivot axis that is orthogonal to longitudinal axis 14 of connecting element 12 and to longitudinal axis 82' of receiver 80'. Pins 204', 206' prevent receiver 80' from rotating around head 36' and longitudinal axis 82'. Pins 204', 206' are located on opposite sides of head 36' and do not extend through head 36' in order to avoid obstructing lumen 37' extending through bone anchor 32'. Pins 204', 206' pivotally couple receiver 80' to anchor 32' for pivoting movement about head 36' that is limited to the plane defined by the longitudinal axis of receiver 80' and connecting element 12 extending through receiver 80'.

FIGS. 27-28 show another embodiment bone anchor assembly 30" where proximal head 36" of anchor 32" does not include a lumen. Head 36" includes a hole 200" extending completely through head 36" and opening at opposite sides of head 36", and a single pin 204" extending through aligned holes 81", 83" of receiver 80" and hole 200" of head 36". Pin 204" pivotally couples receiver 80" to anchor 32" for pivoting movement about head 36" that is limited to the plane defined by the longitudinal axis of receiver 80" and connecting element 12 extending through receiver 80".

Figure 29:
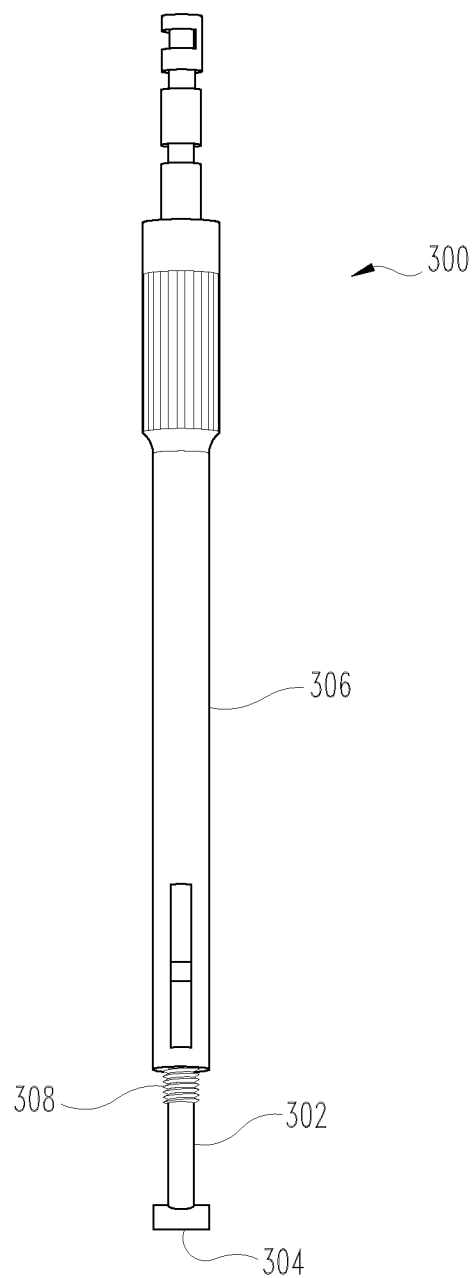
FIG. 29 is a perspective view of a driving tool for inserting a bone anchor assembly into bone.

FIG. 29 shows a driver instrument 300 that can be used to insert and drive the anchor assemblies herein into bone. Driver instrument 300 includes an inner shaft 302 with a distal, cylindrically shaped foot 304 that is elongated along an axis transverse to the longitudinal axis of the instrument to fit within passage 94 of anchor 30 against saddle 220. Driver instrument 300 also includes an outer tubular member 306 positioned around inner shaft 302. Tubular member 306 includes a distal collar 308 spaced proximally from foot 304. Tubular member 306 is rotatable relative to inner shaft 302 to threadingly engage collar 308 with arms 90, 92 of receiver 80 with foot 304 in receiver 80, and press foot 304 against saddle 220 to secure it against head 36 of bone anchor 32. The anchor assembly 30 can then be rotated and threaded into the bone as a rigid, assembled construct with driver instrument 300.

The bone anchor assemblies discussed herein allow adjustment of the angle of the saddle and thus the angle of the connecting element extending through the saddle in a single plane defined by the longitudinal axis of the connecting element and the longitudinal axis of the receiver. The bone anchor assemblies provide a two-piece construct for the receiver and the bone anchor that forms a rigid or semi-rigid bone anchor assembly when the receiver is assembled with the bone anchor while limiting angulation of the saddle in a particular plane. The two piece construct allows the receiver and bone anchor to be comprised of different materials suitable for the expected loading of the components. For example, the receiver can be made from a higher strength material than the material for the bone anchor so that the splaying and other deformations of the receiver can be limited by the higher strength material and so that the side of the receiver can be minimized to limit intrusiveness into the surrounding tissue post-implantation.

Materials for the anchors, receivers, saddles and engaging members disclosed herein can be chosen from any suitable biocompatible material, such as titanium, titanium alloys, cobalt-chromium, cobalt-chromium alloys, or other suitable metal or non-metal material. Connecting element 12 can be made from the same material as one or more of the components of the anchor assembly to which it is engaged, or from a different material. For example, connecting element 12 can be made from PEEK, plastic, titanium or titanium alloy, cobalt-chrome, composite material, or other material that is the same or different from the material of one or more components of the anchor assembly to which is engaged. The anchor assemblies can be sized for placement at any level of the spine and for engagement with any bony portion of the spine. In one particular embodiment, the anchor assemblies are engaged to pedicles of the vertebrae. Of course, it is understood that the relative size of the components of the anchor assemblies can be modified for the particular vertebra (e) to be instrumented and for the particular location or structure of the vertebrae to which the anchor assembly will be engaged.

While the invention has been illustrated and described in detail in the drawings and foregoing description, the same is to be considered as illustrative and not restrictive in character. All changes and modifications that come within the spirit of the invention are desired to be protected.

What is claimed is:

1. A bone anchor assembly, comprising:
   a receiver extending along a central longitudinal axis between a proximal end and an opposite distal end, said receiver including a distal portion defining a receptacle opening at said distal end and a pair of arms extending from said distal portion along said central longitudinal axis on opposite sides of a passage, said pair of arms including inner surfaces facing one another on opposite sides of said passage and outer surfaces, said pair of arms each including a groove extending into a respective inner surface without extending through a respective outer surface, said grooves extending transverse to said central axis and being curved between opposite end surfaces of said arms such that a middle portion of each groove is disposed more distally than opposite ends of said groove, said receiver including a bottom surface extending along said passage between said pair of arms, wherein said passage opens at opposite sides of said receiver between said pair of arms and said receptacle opens into said passage through said bottom surface;
   a bone anchor including a distal bone engaging portion and a head at a proximal end of said distal bone engaging portion, said head including a platform extending from said head comprising a pair of rails, said rails protruding axially from said platform and defining a recess therebetween, said head being positioned in said receptacle with said bone engaging portion in a first orientation relative to said central longitudinal axis of said receiver;
   a saddle positioned in said passage of said receiver adjacent to said bottom surface of said receiver, said saddle being configured to translate within said grooves in said receiver, said saddle including a proximal support surface and a convex distal surface opposite said proximal support surface, said distal surface contacting said pair of rails of said platform as said saddle translates within said grooves and said recess, said proximal support surface being concavely curved between said opposite sides of said saddle and linear between said ends of said saddle;

a connecting element extending along a central longitudinal axis, said connecting element being located in said passage and extending through said opposite sides of said receiver; and an engaging member engaged to said pair of arms to secure said connecting element against said proximal support surface of said saddle, wherein said saddle engages said receiver and is limited to movement in said receiver in a single plane defined by said central longitudinal axis of said receiver and said central longitudinal axis of said connecting element while said bone engaging portion remains in said first orientation.

2. The bone anchor assembly of claim 1, wherein said saddle is movable in said receiver so that said support surface parallels said longitudinal axis of said connecting element in orientations of said longitudinal axis of said connecting element that vary up to 30 degrees from an orthogonal orientation of said longitudinal axis of said connecting element with said central longitudinal axis of said receiver.

3. The bone anchor assembly of claim 1, wherein:
said grooves in said inner surfaces are curved between opposite ends of a respective one of said pair of arms so that said curve includes a most distal portion at said central longitudinal axis and said groove is curved proximally from said most distal portion toward said opposite ends of said respective arm; and
said saddle including at least one ear on each side of said proximal support surface that are positioned in a respective one of said grooves, said ears being slidably movable along said respective one of said grooves.

4. The bone anchor assembly of claim 3, wherein said saddle includes a pair of ears extending from each side thereof with each of said ears of said side located at an end of said saddle and each of said sides is concavely curved between said pair of ears thereof.

5. The bone anchor assembly of claim 1, wherein:
said head of said bone anchor includes a rectangular shape with a pair of longer sides extending toward said pair of arms of said receiver and a pair of shorter sides extending between opposite ends of said longer sides, said shorter sides being convexly curved between said longer sides; and
said receptacle of said receiver includes a rectangular shape distally of said opening into said passage, said rectangular shape including a pair of longer sides extending toward said pair of arms of said receiver and a pair of shorter sides extending between opposite ends of said longer sides, said shorter sides being convexly curved between said longer sides and said sides of said receptacle are sized to accept said proximal head of said anchor member therein.

6. The bone anchor assembly of claim 5, wherein said opening into said passage from said receptacle is square-shaped and said platform extending from said head extends through said square-shaped opening into said passage, and said distal surface of said saddle contacts said platform of said anchor member.

7. The bone anchor assembly of claim 6, wherein said pair of rails extends along said longer sides of said head of said bone anchor and a groove between said pair of rails.

8. The bone anchor assembly of claim 1, wherein said proximal support surface and said distal surface of said saddle extend between opposite ends of said saddle, said saddle further including a tooth at each of said ends projecting distally from said distal surface of said saddle, wherein a respective one of said teeth contacts said proximal head of said bone anchor when said saddle and said connecting member are oriented in said receiver at a maximum angle from an orthogonal orientation of said longitudinal axis of said connecting element with said central longitudinal axis of said receiver.

9. The bone anchor assembly of claim 1, wherein:
said distal portion of said receiver includes first and second holes on opposite sides thereof that extend transversely to said central longitudinal axis of said receiver into said receptacle of said receiver;
said head of said anchor includes at least one opening in a side thereof; and at least one pin extends through said first and second holes and into said at least one opening of said head to pivotally coupled said receiver to said head of said bone anchor about a pivot axis defined by said at least one pin.

10. The bone anchor assembly of claim 9, wherein said pivot axis is orthogonal to said longitudinal axis of said connecting element and said central longitudinal axis of said receiver.

11. The bone anchor assembly of claim 1, wherein said bone anchor is fixed in said first orientation relative to said receiver when positioned in said receptacle of said receiver and said receiver is made from a first material and said bone anchor is made from a second material, said first material being different from said second material.

12. The bone anchor assembly of claim 1, wherein:
said bone anchor comprises a transition portion between said head and said distal bone engaging portion having an even outer surface;
said bone anchor assembly comprises a retaining member comprising a circular, ring-shaped body having a gap, said retaining member having an inner surface configured to engage said transition portion; and
an inner surface of said receiver comprises a circumferential recess adjacent said receptacle having a maximum width that is greater than a maximum width of said receptacle, said recess being configured for disposal of said retaining member such that an outer surface of said retaining member engages an inner surface of said recess to couple said bone anchor to said receiver.

13. The bone anchor assembly of claim 1, wherein said receptacle includes elongated, linear sides extending between said arms and connected with concavely rounded shorter sides extending between the linear sides, said receptacle further includes a square shaped opening extending through a bottom surface of said receiver, wherein said head prevents said rotation of said receiver about said central axis relative to said head while permitting side-to-side toggling or receiver in a direction toward said rounded sides and in a direction toward said linear sides when said head is positioned in said receptacle.

14. A bone anchor assembly, comprising:
a receiver extending along a central longitudinal axis between a proximal end and an opposite distal end, said receiver including a distal portion defining a receptacle opening at said distal end and a pair of arms extending from said distal portion along said central longitudinal axis on opposite sides of a passage with said passage opening at opposite sides of said receiver, said pair of arms including inner surfaces facing one another on opposite sides of said passage and outer surfaces, said pair of arms each including a groove extending into a respective inner surface without extending through a respective outer surface, said grooves extending transverse to said central axis and being curved between opposite end surfaces of said arms such that a middle portion of each groove is disposed more distally than opposite ends of said groove, said receiver including a bottom surface extending along said passage between said pair of arms, wherein said receptacle opens into said passage through said bottom surface;

a bone anchor including a distal bone engaging portion and a head at a proximal end of said distal bone engaging portion, said head being positioned in said receptacle with said bone engaging portion extending through said distal end of said receiver in a first orientation relative to said central longitudinal axis of said receiver, said head including a platform extending from a proximal surface of said head through said opening of said receptacle into said passage, said platform comprising a pair of rails protruding axially from said platform and defining a recess therebetween;

a saddle positioned in said passage of said receiver adjacent to said bottom surface of said receiver, said saddle including a proximal support surface and a convex distal surface opposite said proximal support surface, said saddle being configured to translate within said grooves in said receiver, said distal surface contacting said pair of rails of said platform as said saddle translates within said grooves and said recess;

a connecting element extending along a central longitudinal axis, said connecting element being located in said passage against said proximal support surface of said saddle and extending through said opposite sides of said receiver; and an engaging member engaged to said pair of arms to secure said connecting element against said proximal support surface of said saddle.

15. The bone anchor assembly of claim 14, wherein said saddle is movable in said receiver in a single plane defined by said central longitudinal axis of said receiver and said central longitudinal axis of said connecting element while said bone engaging portion remains in said first orientation.

16. The bone anchor assembly of claim 14, wherein:
said head of said bone anchor includes a rectangular shape with a pair of longer sides extending toward said pair of arms of said receiver and a pair of shorter sides extending between opposite ends of said longer sides, said shorter sides being convexly curved between said longer sides; and
said receptacle of said receiver includes a rectangular shape distally of said opening into said passage, said rectangular shape including a pair of longer sides extending toward said pair of arms of said receiver and a pair of shorter sides extending between opposite ends of said longer sides, said shorter sides being convexly curved between said opposite sides and said sides of said receptacle are sized to accept said proximal head of said anchor member therebetween.

17. The bone anchor assembly of claim 16, wherein said opening of said receptacle into said passage is square-shaped and said platform extending from said head of said anchor member extends through said square-shaped opening into said passage.

18. The bone anchor assembly of claim 16, wherein said receiver includes a lip extending from opposite sides of said platform toward said shorter sides of said head to prevent said head from passing through said opening of said receptacle.

19. A bone anchor assembly, comprising:
a receiver extending along a central longitudinal axis between a proximal end and an opposite distal end, said receiver including a distal portion defining a receptacle opening at said distal end and a pair of arms extending from said distal portion along said central longitudinal axis on opposite sides of a passage with said passage opening at opposite sides of said receiver, said pair of arms including inner surfaces facing one another on opposite sides of said passage and outer surfaces, said pair of arms each including a groove extending into a respective inner surface without extending through a respective outer surface, said grooves extending transverse to said central axis and being curved between opposite end surfaces of said arms such that a middle portion of each groove is disposed more distally than opposite ends of said groove, said receiver including a bottom surface extending along said passage between said pair of arms, wherein said receptacle opens into said passage;

a bone anchor including a distal bone engaging portion and a head at a proximal end of said distal bone engaging portion, said head including a platform extending from said head comprising a pair of rails protruding axially from said platform and defining a recess therebetween, said head being positioned in said receptacle with said bone engaging portion extending through said distal end of said receiver in a first orientation relative to said central longitudinal axis of said receiver;

a saddle positioned in said passage of said receiver adjacent to said bottom surface of said receiver, said saddle including a proximal support surface and a convex distal surface opposite said proximal support surface, said saddle being configured to translate within said grooves in said receiver, said distal surface contacting said pair of rails as said saddle translates within said grooves in said receiver and said recess in said bone anchor, wherein said proximal support surface and said distal surface extend between opposite ends of said saddle and each of said opposite ends includes a tooth extending distally from said distal surface of said saddle;

a connecting element extending along a central longitudinal axis, said connecting element being located in said passage and extending through said opposite sides of said receiver; and an engaging member engaged to said pair of arms to secure said connecting element against said proximal support surface of said saddle, wherein a respective one of said teeth of said saddle contacts said proximal head of said bone anchor when said saddle and said connecting element are pivoted in said receiver to a maximum angle from an orthogonal orientation of said central longitudinal axis of said connecting element with said central longitudinal axis of said receiver.

20. The bone anchor assembly of claim 19, wherein:
said head of said bone anchor includes a rectangular shape with a pair of longer sides extending toward said pair of arms of said receiver and a pair of shorter sides extending between opposite ends of said longer sides, said shorter sides being convexly curved between said longer sides;
said receptacle of said receiver includes a rectangular shape adjacent to said opening into said passage, said rectangular shape including a pair of longer sides extending toward said pair of arms of said receiver and a pair of shorter sides extending between opposite ends of said longer sides, said shorter sides being convexly curved between said longer sides and said sides of said receptacle are sized to accept said proximal head of said anchor member therebetween;

said opening of said receptacle into said passage is square-shaped;

said platform extending from said head extends from a proximal surface of said head through said square-shaped opening into said passage; and said respective one of said teeth said saddle contacts a side of said platform extending from said head when pivoted to said maximum angle.

* * * * *